United States Patent [19]
Reilly

[11] 3,987,068
[45] Oct. 19, 1976

[54] OXIDATION OF MONOHYDROXY ARYL COMPOUNDS TO 1,4-QUINONES

[75] Inventor: Edward Leo Reilly, Wilmington, Del.

[73] Assignee: E. I. Du Pont de Nemours and Company, Wilmington, Del.

[22] Filed: July 28, 1975

[21] Appl. No.: 599,643

[52] U.S. Cl. .................... 260/396 R; 260/47 ET; 260/396 N
[51] Int. Cl.² .................. C07C 49/64; C07C 49/66
[58] Field of Search ................ 260/396 R, 396 N

[56] References Cited
UNITED STATES PATENTS
3,210,384  10/1965  Hay ............................ 260/396 N Primary Examiner—Vivian Garner

[57] ABSTRACT

A monohydroxy aryl compound, e.g., phenol or α-naphthol, or a mono- or dialkyl phenol or α-naphthol, is oxidized to the corresponding monomeric 1,4-quinone in a nitrile solution containing a soluble copper-nitrile complex catalyst by reaction with an oxygen-containing gas at a temperature in the range of about from 0° to 100° C. and under an oxygen partial pressure of about from 7 to 200 atmospheres, and at least about 20 atmospheres when the compound being oxidized is phenol. The elevated oxygen pressure favors conversion to the monomeric quinone, as contrasted to polymeric products.

16 Claims, No Drawings

OXIDATION OF MONOHYDROXY ARYL COMPOUNDS TO 1,4-QUINONES

BACKGROUND OF THE INVENTION

1. Field of the Invention

The present invention relates to the oxidation of monohydroxy mono- and bicyclic aryl compounds, e.g., phenol, to form monomeric 1,4-quinones, e.g., p-benzoquinone.

2. Description of the Prior Art

The oxidation of disubstituted phenols by means of oxygen in the presence of copper salt complexes with amines, nitriles, or tertiary amides has been widely reported to give self-condensation products, i.e., polyphenylene ethers and/or diphenoquinones. A. S. Hay et al. (J. Am. Chem. Soc. 81, 6335–6 (1959)) described the oxidative coupling of 2,6-disubstituted phenols in an organic solvent containing an amine (pyridine) and a copper salt as a catalyst. With small alkyl substituents on the phenol, carbon-oxygen coupling occurred and linear polyphenylene ethers were obtained. With bulky substituents, carbon-carbon coupling occurred and the diphenoquinone was obtained. Hay later noted (J. Polymer Sci 58, 583 (1962)) that the oxidation of simple monohydric phenols had generally yielded very complex products unless the phenol had been substituted in both ortho positions. In the same paper (p. 585) Hay mentioned that when phenol itself was treated with oxygen in pyridine solution in the presence of copper (I) chloride, a complex tarry residue was formed.

In U.S. Pat. No. 3,306,874, Hay reported that primary and secondary aliphatic amines can be used in forming an amine-basic cupric salt complex for the oxidation of monohydric, monocyclic phenols to various self-condensation products providing the phenols are substituted in the 2- and 6-position. Another patent to Hay, U.S. Pat. No. 3,210,384, describes the oxidation of a 2,6-disubstituted phenol in the presence of a complex of a basic cupric salt and a nitrile or tertiary amide. 3,3',5,5'-Tetrasubstituted diphenoquinone was obtained.

Braxton et al. (U.S. Pat. No. 3,213,114) described oxidizing certain 2,4,6-trialkyl phenols (4 to 12 carbon alkyl groups) to 2,6-dialkyl-p-benzoquinones by means of oxygen and a catalyst, preferably a cuprous chloride complex of an amine. The patentees concluded that the presence of a hydrocarbon radical having a tertiary configuration in both positions ortho to the hydroxyl group as well as in the para position was necessary for the successful, practical oxidation of the phenol to the p-benzoquinone.

Japanese Application Publication 36,641/74, published Apr. 5, 1974, describes the oxidation of 2,3,6-trimethylphenol by means of oxygen in the presence of a cupric salt dissolved in a nitrile or tertiary amide to give chiefly trimethyl-p-benzoquinone when the molar ratio of copper salt to trimethylphenol is high, e.g., about 1/1, or a mixture of the benzoquinone with polyphenylene oxide at lower molar ratios.

German Pat. No. 2,221,624 (May 2, 1972) teaches that methyl-substituted phenols (mono-, di-, tri-, or tetramethyl) can be oxidized to the corresponding quinones by means of oxygen in the presence of copper and halogen ions provided that complexing agents are absent or limited. It is stated that especially when the phenol has only one or two methyl groups, the yield of monomeric quinone decreases as the amount of complexing agent increases.

The catalytic oxidation of phenol to p-benzoquinone by means of oxygen recently has been described in U.S. Pat. Nos. 3,859,317 and 3,870,731, both of common filing date and inventer. In the process of U.S. Pat. No. 3,859,317, a cobalt(II) or manganese(II) coordination catalyst is used in combination with an alkanol, benzonitrile, hexamethyl phosphoric triamide, N-alkyl-substituted amide, or sulfoxide solvent. In the process of U.S. Pat. No. 3,870,731, which is applied also to the oxidation of alkyl- or halo-substituted phenols, a copper(I), copper(II), or metallic copper catalyst and a thiocyanate, cyanate, cyanide, or halogen ion catalyst promoter are used in combination with a water, N-alkyl-substituted amide, alcohol, or sulfoxide solvent. In these systems the amount of phenol reacted generally is small even after long reaction times.

To summarize, copper complex cataysts appear to be superior with respect to level of activity, as evidenced by conversions achieved and reaction times required, in the oxidation of phenols by means of oxygen. However, the prior art teaches that, with these catalysts, complex products are obtained unless the phenol is substituted in the 2- and 6-positions, and that complex tarry residues are obtained with unsubstituted phenol. The prior art also teaches that, with these catalysts, 2,6-disubstituted phenols give self-condensation products, i.e., polyphenylene ethers and/or diphenoquinones. In copper complex catalyst systems, uncoupled products have been reported only in the case of the oxidation of trialkyl-substituted phenols, but large quantities of polyphenylene oxide also were obtained unless the molar ratio of copper salt to the phenol was high. In German Pat. No. 2,221,624, complexing agents were described as being inimical to the formation of monomeric quinones in oxidations of mono-, di-, tri-, or tetramethyl phenols in the presence of copper and halogen ions, and such agents were described as preferably being absent, or at least present only in limited amounts.

1,4-Quinones are desirable as intermediates to hydroquinones, which find utility as antioxidants, reducing agents, polymer intermediates, etc.

SUMMARY OF THE INVENTION

The present invention provides a process wherein the oxidation of a monohydroxy aryl compound, e.g., phenol, α-naphthol, or certain of their mono- and dialkyl-substituted derivatives, is carried out in copper complex systems in a manner such as to favor the formation of the corresponding 1,4-quinone or, conversely, to suppress the formation of polyarylene ethers and dipheno- and dinaphthoquinones.

The present process comprises contacting a monohydroxy aryl compound unsubstituted in the position para to the hydroxyl group and selected from the group consisting of phenols, α-naphthols, and mono- and dialkyl phenols and α-naphthols, in solution in a nitrile, e.g., acetonitrile, containing a copper salt with an oxygen-containing gas at a temperature in the range of about from 0° to 100° C., preferably up to about 75° C., and under an oxygen partial pressure of about from 7 to 200, preferably 14 to 100, atmospheres, the nitrile and the copper salt together forming a complex which is soluble in the reaction system.

In a preferred embodiment of the process, phenol in a nitrile solution containing a complexing copper salt is oxidized to p-benzoquinone at a temperature in the range of about from 20° to 75° C. and under an oxygen partial pressure of about from 20 to 100 atmospheres.

DETAILED DESCRIPTION

It has been found that, with respect to the competing reactions which can take place in the oxidation of the above-specified phenols and napthols in copper complex catalyst systems, the dominant reaction that will occur in any given case is influenced significantly by the partial pressure of the oxygen. More specifically, it has been found that an oxygen partial pressure of at least about 7 atmospheres is necessary to direct the reaction toward the dominant production of the uncoupled para-quinone, and that the yield of this product increases, while the yield of polymeric products decreases, with increasing oxygen partial pressure. This directive effect is in contradistinction to an effect on the overall consumption of the phenol or naphthol or on the reaction rate. Thus, a given pressure may be high enough to convert a high percentage of the phenol or naphthol to products at a reasonable rate but insufficient to direct the reaction toward the formation of uncoupled para-quinone.

In the prior art processes for oxidizing dialkyl phenols in copper complex systems, which processes gave polyphenylene ethers and/or diphenoquinones (U.S. Pat. Nos. 3,210,384 and 3,306,874), the use of elevated pressure was not recommended. Elevated pressure is stated either as being ineffective (Japanese Publication 36,641/74), unnecessary, or only as enhancing reaction time and the amount of the phenol converted (U.S. Pat. No. 3,213,114), in the art on oxidizing other alkyl phenols to p-benzoquinones. In the latter case, the formation of the benzoquinone is attributed to the presence of a specific type of hydrocarbon substituent in each of three positions on the phenol. The present process is based on the unexpected finding that substitution in this manner or the absence of complexing agents is not required if the oxygen partial pressure is sufficiently high.

In the present process, the compound which undergoes oxidation to the 1,4-quinone is a monohydroxysubstituted monocyclic or bicyclic aryl compound, i.e., phenol or α-naphthol, or a mono- or dialkyl derivative thereof wherein the carbon atom in the position para to the hydroxyl-bearing carbon atom is unsubstituted. Thus, the phenol can be a monoalkyl phenol having an alkyl group attached to the 2-, 3-, 5-, or 6-carbon, e.g., o- or m-cresol; or a dialkyl phenol having the alkyl groups in the 2,3-, 2,5-, 2,6-, or 3,5-position, e.g., 2,3-, 2,5-, 2,6-, or 3,5-dimethylphenol. The α-naphthol can be a monoalkyl naphthol having an alkyl group attached to the 2-, 3-, 5-, 6-, 7-, or 8-carbon, e.g., 3-methyl-α-naphthol; or a dialkyl naphthol having the alkyl groups attached to any two carbon atoms exclusive of the 4-carbon. Although the size of the alkyl group(s) per se appears to have no significant effect on the products obtained from the present process and such groups can contain, for example, from 1 to about 12 carbon atoms, phenols and naphthols having smaller alkyl groups, e.g., 1 to 4 carbon atom alkyl groups, and especially methyl groups, are more readily available, and on this basis are preferred. The alkyl groups in dialkyl compounds can be the same or different. Other substituents which are nonreactive under the reaction conditions, e.g., halo or alkoxy groups, also may be present, provided the carbon atom which is in the position para to the hydroxyl-bearing carbon atom is free.

The oxidation of the phenol or α-naphthol takes place in a nitrile solution which contains a cuprous or cupric salt. Any nitrile and any cuprous or cupric salt which together form a complex that is soluble in the reaction medium can be used. Such complexes are well-known in the art and are described, for example in J. Am. Chem. Soc. 91, 56–62 (1969). Specific types of nitriles that can be employed are the aliphatic and cycloaliphatic nitriles, e.g., acetonitrile, propionitrile, and butyronitrile, including those containing two or more cyano groups, e.g., adiponitrile, glutaronitrile, and 2-methylglutaronitrile; and aromatic nitriles, e.g., benzonitrile and tolunitrile. Mixtures of nitriles can be used.

Typical examples of the copper salts suitable for the process are cuprous chloride, cupric chloride, cuprous bromide, cupric bromide, and cupric nitrate. Cupric acetate can be used provided a source of chloride or bromide ion, e.g., hydrochloric or hydrobromic acid, is present. Mixtures of copper salts can be used.

The nitrile solution of the phenol or α-naphthol and of the copper complex is contacted with an oxygen-containing gas, e.g., oxygen itself, air, or another mixture of oxygen diluted with an inert gas, under an oxygen partial pressure of at least about 7, and preferably at least about 14, atmospheres. As stated previously, an elevated oxygen partial pressure is critical to the production of the monomeric quinone. As is shown in the following examples (Example 2), for a given reaction system with substantially the same amount of phenol consumed, the amount of phenol converted to p-benzoquinone increases dramatically with the oxygen partial pressure. The minimum pressure required to convert a major portion of the phenol or α-naphthol to the corresponding 1,4-quinone will vary depending on the particular starting material, the minimum pressure being lower as the degree of phenol substitution is higher. Thus, the minimun oxygen partial pressure will be about 7 atmospheres, preferably about 14 atmospheres, for the dialkyl phenols and α-naphthol; about 14 atmospheres for the monoalkyl phenols; and about 20 atmospheres, preferably about 35 atmospheres, for phenol. Oxygen partial pressures as high as about 200 atmospheres can be used, although there appears to be no advantage in terms of monomeric quinone yield in exceeding about 100 atmospheres. Generally, in terms of best yields and practicability, a particularly preferred oxygen partial pressure range is about from 14 to 70 atmospheres. When air is used as the oxidizing agent, air pressures of about 70 to 200 atmospheres are preferred.

The process of this invention is effected at moderate temperatures, generally in the range of about from 0° to 100° C. To achieve nearly complete consumption of the phenol or α-naphthol within reasonable reaction times, e.g., in about 1 hour, a temperature above about 30° C. is preferred in a batch-type operation. Temperatures above about 100° C., and preferably above about 75° C., are not employed in this mode of operation to avoid extensive by-product formation. In continuous operation, a preferred temperature range in terms of quinone yield and feasible holdup times is about from 5° to 40° C., about from 20° to 30° C. being especially preferred.

The presence of water in the reaction system is helpful in controlling the reaction rate and avoiding by-product formation due to over-oxidation, particularly in the case of the alkyl-substituted phenols and naphthols. The greater the number of substitutents in the starting material, the more water that can be used. Up to about 50 percent by volume of water, based on the total volume of nitrile solution, can be used in some cases, although up to about 30 percent by volume usually is adequate.

The amount of copper salt used should be sufficient to provide a ratio of about from 5 to 25 moles of the phenol or naphthol per mole of copper salt. With higher molar ratios, the amount of copper salt is so small that the phenol or naphthol consumption, as well as the amount thereof converted to the 1,4-quinone, drops. No advantage in terms of yield is achieved in using an amount of copper salt in excess of that which gives about a 5/1 molar ratio of phenol or naphtol to copper salt.

The concentration of the nitrile solution of the phenol or naphthol can vary widely. There is no minimum concentration to be adhered to except for that which is dictated by practical considerations. At higher concentrations, e.g., at about 50% or more of the phenol or naphthol based on the weight of the nitrile, the phenol or naphthol consumption tends to decrease. Therefore, a preferred concentration range is about from 10 to 50%. The molar ratio of nitrile to copper salt is in excess of about 10/1, and often in excess of about 100/1.

The solution of the phenol or α-naphthol in the nitrile containing the copper complex is contacted with the oxygen-containing gas usually for at least about 10 minutes, the specific time required in any given case depending on the reaction temperature and the molar ratio of phenol or α-naphthol to copper salt. Reaction times longer than about one hour usually are not required to achieve essentially complete consumption of the phenol or α-naphthol.

The following examples illustrate various embodiments of the present process. The conversion is the moles of the 1,4-quinone obtained per mole of monohydroxy compound charged to the reactor; the yield is the moles of the 1,4-quinone obtained per mole of monohydroxy compound consumed.

EXAMPLE 1

Phenol (20.0 grams; 0.213 mole) and 1.4 grams of cuprous chloride (0.014 mole) are dissolved in 100 milliliters of acetonitrile at 40° C. in a 400-milliliter stainless steel shaker tube reaction vessel. The shaker tube then is pressurized with oxygen to 70 atmospheres and heated, with agitation, at 40° C. for 60 minutes. The vessel then is cooled down to about room temperature and vented. After the acetonitrile has been distilled off and the copper salt precipitated out by the addition of ether, a solution is obtained which contains 17.0 grams of p-benzoquinone and 1.4 grams of phenol (93% phenol consumed; conversion to p-benzoquinone: 74%, yield of p-benzoquinone: 80%).

CONTROL EXPERIMENT

The procedure described in Example 1 is repeated with the exception that the amount of phenol used is 25 grams, 250 milliliters of benzonitrile is substituted for the 100 milliliters of acetonitrile, the amount of cuprous chloride used is 5 grams, the temperature is 55° C., and the oxygen pressure is atmospheric. Oxygen is fed into the solution at a rate of 150 milliliters per minute. There is no conversion to p-benzoquinone after 30 minutes even when the temperature is increased to 74° C.; after about 5 hours, the conversion to p-benzoquinone is about 1%.

EXAMPLE 2

The procedure described in Example 1 is repeated with the exception that the amount of phenol used is 10.0 grams, the temperature is 60° C., the reaction time is 2 hours, and 2 grams of cuprous bromide is substituted for the cuprous chloride. Under these conditions, when the oxygen partial pressure is 70 atmospheres the phenol consumption is 99+%; the conversion to, and yield of, p-benzoquinone is 74%.

As the pressure is lowered in this system, the yield of p-benzoquinone drops despite a 90+% phenol consumption (i.e., in the pressure range studied, the pressure affects the product distribution as contrasted to the phenol consumption). At 21 atmospheres, with a phenol consumption of 99+%, p-benzoquinone is still the major product (52% conversion and yield). At 12.6 atmospheres, with 92% of the phenol consumed, the yield of p-benzoquinone is 42% and the conversion to p-benzoquinone is 39%.

At a pressure of 6.3 atmospheres, and with 1.4 grams of cuprous chloride instead of 2 grams of cuprous bromide, the yield and conversion are only 20% and 19%, respectively, although 95% of the phenol is consumed. The product is chiefly a complex polymeric composition.

EXAMPLES 3–10

The procedure described in Example 1 is followed with the use of different copper salts to form the complex catalyst. The conditions and results are shown in the following table.

| Ex. | Phenol (g.) | Copper Salt (g.) | Acetonitrile (ml.) | Temp. (° C.) | $O_2$ Pressure atm. | Reaction Time (min.) | % Phenol Consumed | % Conversion to p-Penzoquinone | % Yield of p-Penzoquinone |
|---|---|---|---|---|---|---|---|---|---|
| 3 | 15 | CuCl (1.0) | 50 | 50 | 105 | 60 | >99 | 78 | 78 |
| 4 | 15 | CuCl (0.5) + Cu(OAc)$_2$.H$_2$O (1) | 50 | 60 | 105 | 60 | >99 | 78 | 78 |
| 5 | 15 | CuCl$_2$.2H$_2$O (1.7) | 50 | 50 | 105 | 30 | 85 | 66 | 78 |
| 6 | 15 | CuCl (0.5) + CuCl$_2$.2H$_2$O (0.9) | 50 | 50 | 105 | 60 | 90 | 70 | 77 |
| 7 | 10 | CuBr (1.0) | 100 | 70 | 70 | 60 | >99 | 78 | 78 |
| 8 | 15 | CuBr$_2$ (2.2) | 50 | 60 | 70 | 60 | 93 | 59 | 64 |
| 9 | 15 | Cu(OAc)$_2$.H$_2$O (2.0) + HCl (0.18) | 50 | 50 | 105 | 30 | 63 | 54 | 86 |
| 10 | 10 | Cu(NO$_3$)$_2$.3H$_2$O (1.7) | 100 | 60 | 70 | 60 | 77 | 36 | 47 |

EXAMPLE 11

The procedure of Example 7 is followed except that the reaction temperature is 60° C. and the amount of phenol used is 10.0 grams. The yield of p-benzoquinone is 84% at a phenol consumption of 83% (70% conversion to p-benzoquinone).

Under the same conditions, but at 70° C., only 46% of the phenol is consumed when 0.5 gram of cuprous bromide is used, giving a molar ratio of phenol to cuprous ion of 30/1 (44% yield of and 20% conversion to p-benzoquinone), and less than 10% of the phenol is consumed when 0.1 gram of cuprous bromide is used (at 60° C.), giving a phenol/cuprous ion molar ratio of 150/1.

EXAMPLE 12

Operating the reaction described in Example 1 with 30 grams of phenol gives the following results at different molar ratios of phenol to cuprous chloride:

| Expt. | CuCl (g.) | Phenol/Cu$^+$ Molar Ratio | % Phenol Consumed | % Conversion to P-Benzoquinone | % Yield of P-Benzoquinone |
|---|---|---|---|---|---|
| a | 2.8 | 10/1 | 90 | 61 | 68 |
| b | 2.1 | 15/1 | 92 | 67 | 73 |
| c | 1.4 | 20/1 | 73 | 51 | 70 |

EXAMPLE 13

When the procedure described in Example 12(b) is repeated except that 45 grams of phenol and 3.1 grams of cuprous chloride are used and the oxygen partial pressure is 63 atmospheres, the yield of p-benzoquinone remains high (75%) although there is a drop in the amount of phenol consumed (75%). The conversion to p-benzoquinone is 56%.

EXAMPLE 14

Carrying out the procedure described in Example 1 at 50° C. and with 30 grams of phenol results in a 71% consumption of phenol and a 65% yield of (and 46% conversion to) p-benzoquinone after a 15-minute reaction; an 81% consumption (52% conversion and 64% yield) after 30 minutes; and a 94% consumption (57% conversion and 60% yield) after 60 minutes.

EXAMPLE 15 a. When the procedure described in Example 1 is repeated except that a temperature of 50° C. is employed, the consumption of phenol is 97%, with a p-benzoquinone yield and conversion of 75 and 73%, respectively.

When a temperature of 30° C. and 30 grams of phenol are used, the phenol consumption is 83%, with a p-benzoquinone yield and conversion of 75% and 62%, respectively. With this phenol concentration, when the temperature is 40° C., the phenol consumption is 92% (73 and 67% p-benzoquinone yield and conversion, respectively).

b. When the procedure described in Example 1 is repeated except that the oxygen pressure is 105 atmospheres and the amount of phenol used is 30 grams, 79% of the phenol is consumed (81% and 64% p-benzoquinone yield and conversion, respectively) at 30° C., and more than 98% consumed (77% p-benzoquinone yield and conversion) at 60° C.

EXAMPLE 16 a. Adiponitrile is used instead of acetonitrile in the procedure described in Example 1. The oxygen pressure is 105 atmospheres, and 15 grams of phenol are used. After 20 minutes, 88% of the phenol is consumed. The yield of p-benzoquinone is 67%; the conversion to p-benzoquinone is 59%.

b. Benzonitrile is substituted for adiponitrile in the procedure described in (a). After 10 minutes, 49% of the phenol has been converted to p-benzoquinone.

EXAMPLES 17–23

In these examples, a different monohydroxy-substituted aromatic hydrocarbon is substituted for the phenol in Example 1. In each case, 50 milliliters of acetonitrile is used. The conditions and results are shown in the following table.

| Ex. | Hydroxy Compound (Wt., in g.) | H$_2$O Added (ml.) | Molar Ratio Hydroxy Compound to Cu Salt* | Temp. (° C.) | O$_2$ Pressure (atm.) | Reaction Time (min.) | % Hydroxy Compound Consumed | 1,4-Quinone Produced (% Yield, % Conversion) |
|---|---|---|---|---|---|---|---|---|
| 17 | o-Cresol (15) | 6 | 12.5 | 50 | 105 | 20 | 93 | 2-Methylbenzoquinone (74, 69) |
| 18 | m-Cresol (15) | 0 | 12.5 | 40 | 94.5 | 20 | 99+ | 2-Methylbenzoquinone (67, 67) |
| 19 | 2,5-Dimethylphenol (5) | 20 | 10 | 50 | 29.4 | 20 | 99+ | 2,5-Dimethylbenzoquinone (82, 82) |
| 20 | 2,3-Dimethylphenol (5) | 20 | 10 | 50 | 29.4 | 20 | 99+ | 2,3-Dimethylbenzoquinone (84, 84) |
| 21 | 3,5-Dimethylphenol (5) | 20 | 10 | 50 | 29.4 | 20 | 99 | 2,6-Dimethylbenzoquinone (96, 95) |
| 22 | 2,6-Dimethylphenol (10) | 0 | 5 | 40 | 33.3 | 30 | 99+ | 2,6-Dimethylbenzoquinone (86, 86) |
| 23 | α-Naphthol (7.5) | 10 | 10 | 50 | 28 | 20 | 99+ | 1,4-Naphthoquinone (61, 61) |

*CuCl in Ex. 17, 18, 19, 20, 21, and 23; CuCl$_2$.2H$_2$O in Ex. 22.

EXAMPLE 24

In a continuous mode of operation of the present process, a solution of phenol and cuprous chloride in acetonitrile is fed continuously at a rate of 0.281 liter per hour into a 0.30-liter tank reactor, and liquid is removed continuously therefrom so as to maintain a liquid volume of 0.19 liter in the reactor. The solution fed to the reactor contains, per liter, 38.0 grams of phenol, 11.0 grams of cuprous chloride, and 30.0 grams of benzonitrile (as an internal analytical standard), and the balance is acetonitrile. The liquid in the reactor is stirred continuously.

Compressed air is also fed continuously into the reactor at a rate of 33 liters per hour (S.T.P.) through a sparger located at the bottom of the reactor. Vapor is removed continuously so as to maintain an air pressure of 210 atmospheres. The temperature in the reactor is maintained at 25° C.

At steady state, 47.1% of the phenol fed is consumed, 36.2% of the phenol fed being converted to p-benzoquinone, constituting a 76.9% yield of p-benzoquinone.

I claim:

1. A process for preparing 1,4-benzoquinones or naphthoquinones comprising contacting a monohydroxy aryl compound unsubstituted in the position para to the hydroxyl group and selected from the group consisting of phenol, α-naphthol, and mono- and dialkyl phenols and α-naphthols, in solution in a nitrile containing a copper salt with an oxygen-containing gas at a temperature in the range of about from 0° to 100° C. and under an oxygen partial pressure of about from 7 to 200 atmospheres, said phenol, α-naphthol, or mono- or dialkyl phenol or α-naphthol optionally being alkoxysubstituted and the alkyl substituents in said mono- or dialkyl phenol or α-naphthol containing 1 to 12 carbon atoms, said nitrile and said copper salt together forming a complex which is soluble in the reaction system, and said copper salt being selected from the group consisting of cuprous chloride, cupric chloride, cuprous bromide, cupric bromide, cupric nitrate, and cupric acetate with the proviso that a source of chloride or bromide ion is present when said copper salt is cupric acetate.

2. A process of claim 1 wherein said monohydroxy aryl compound is an o- or m-alkyl phenol and said oxygen partial pressure is at least about 14 atmospheres.

3. A process for preparing 1,4-benzoquinones or naphthoquinones comprising contacting a monohydroxy aryl compound unsubstituted in the position para to the hydroxyl group and selected from the group consisting of phenol, α-naphthol, and mono- and dialkyl phenols and α-naphthols, in solution in a nitrile containing a copper salt with an oxygen-containing gas at a temperature in the range of about from 0° to 100° C. and under an oxygen partial pressure of about from 7 to 200 atmospheres, said phenol, α-naphthol, or mono- or dialkyl phenol or α-naphthol optionally being alkoxysubstituted and the alkyl substituents in said mono- or dialkyl phenol or α-naphthol containing 1 to 12 carbon atoms, said nitrile being selected from the group consisting of acetonitrile, propionitrile, butyronitrile, adiponitrile, glutaronitrile, 2-methylglutaronitrile, benzonitrile, and tolunitrile, and said copper salt being selected from the group consisting of cuprous chloride, cupric chloride, cuprous bromide, cupric bromide, cupric nitrate, and cupric acetate, with the proviso that a source of chloride or bromide ion is present when said copper salt is cupric acetate.

4. A process of claim 3 wherein said monohydroxy aryl compound is selected from the group consisting of phenol, o-alkyl phenols, and m-alkyl phenols.

5. A process of claim 3 wherein said solution of monohydroxy aryl compound is contacted with said oxygen-containing gas in a continuous manner, and said temperature is in the range of about from 5° to 40° C.

6. A process of claim 5 wherein said oxygen-containing gas is air.

7. A process of claim 3 wherein said monohydroxy aryl compound is contacted with said oxygen-containing gas at a temperature in the range of about from 20° to 75° C. and under an oxygen partial pressure of about from 14 to 100 atmospheres.

8. A process of claim 7 wherein the molar ratio of said monohydroxy aryl compound to said copper salt is in the range of about from 5/1 to 25/1.

9. A process of claim 7 wherein up to about 50 percent by volume of water is present in the nitrile solution, based on the total volume of solution.

10. A process for preparing p-benzoquinone comprising contacting phenol in solution in a nitrile containing a copper salt with an oxygen-containing gas at a temperature in the range of about from 0° to 100° C. and under an oxygen partial pressure of about from 20 to 200 atmospheres, said nitrile and said copper salt together forming a complex which is soluble in the reaction system, said copper salt being selected from the group consisting of cuprous chloride, cupric chloride, cuprous bromide, cupric bromide, cupric nitrate, and cupric acetate with the proviso that a source of chloride or bromide ion is present when said copper salt is cupric acetate.

11. A process of claim 10 wherein said nitrile is selected from the group consisting of acetonitrile, adiponitrile, and benzonitrile.

12. A process of claim 11 wherein said phenol is contacted with said oxygen-containing gas at a temperature in the range of about from 20° to 75° C., and the molar ratio of phenol to said copper salt is in the range of about from 5/1 to 25/1.

13. A process of claim 1 wherein said monohydroxy aryl compound is a dialkyl phenol.

14. A process of claim 13 wherein the alkyl substituents in said dialkyl phenol are methyl groups.

15. A process of claim 14 wherein said dialkyl phenol is 2,6-dimethylphenol.

16. A process of claim 14 wherein said dialkyl phenol is 3,5-dimethylphenol.

* * * * *